United States Patent [19]

Hiraga et al.

[11] Patent Number: 4,879,293
[45] Date of Patent: Nov. 7, 1989

[54] PYRROLS [3,4-8]PYRAZINE DERIVATIVES, THEIR PRODUCTION AND USE AS ANTI-ANXIETY AGENTS

[75] Inventors: Kentaro Hiraga, Nagaokakyo; Yoshiaki Saji, Kawanishi, both of Japan

[73] Assignee: Takeda Chemical Industries, Ltd., Osaka, Japan

[21] Appl. No.: 241,851

[22] Filed: Sep. 8, 1988

Related U.S. Application Data

[62] Division of Ser. No. 832,138, Apr. 23, 1986, Pat. No. 478,191, which is a division of Ser. No. 478,478, Mar. 24, 1983, Pat. No. 4,590,189.

[30] Foreign Application Priority Data

Apr. 2, 1982 [WO] PCT Int'l Appl. ... PCT/JP82/00096
Oct. 7, 1982 [WO] PCT Int'l Appl. ... PCT/JP82/00401
Feb. 5, 1983 [WO] PCT Int'l Appl. ... PCT/JP83/00032

[51] Int. Cl.[4] .............. A61K 31/535; A61K 31/505; A61K 31/50; A61K 31/495; A61K 31/445; A61K 31/44; A61K 31/40; A61K 31/41; A61K 31/47; C07D 401/10; C07D 413/14; C07D 409/14
[52] U.S. Cl. .................................. 514/249; 514/212; 514/234.2; 514/235.2; 514/252; 514/254; 514/300; 514/314; 514/322; 514/365; 514/367; 514/368; 514/370; 540/596; 540/599; 540/600; 544/117; 544/238; 544/295; 544/331; 544/333; 544/350; 544/357; 544/360; 544/362; 544/363; 544/364; 544/368; 544/369; 544/405; 546/122; 546/167; 546/193; 546/198; 546/199; 546/200; 546/270; 548/159; 548/181; 548/453; 548/454; 548/468; 548/470; 548/471; 548/472; 548/482
[58] Field of Search .............. 540/599, 600; 544/117, 544/238, 295, 333, 350, 357, 331; 514/212, 234.2, 249

[56] References Cited

U.S. PATENT DOCUMENTS 4,788,191 11/1988 Hiraga et al. ............... 544/238

FOREIGN PATENT DOCUMENTS 7217852 7/1973 Netherlands ............. 544/350

OTHER PUBLICATIONS

S. Garbriel et al., Chem. Ber. 40, 4850–4861 (1907).
Richard Pater, J. Heterocycl. Chem. 7, 1113–1124 (1970).
Horii et al., J. Org. Chem. 26, 2273–2276 (1961).
Schweizer, Helv. Chim. Acta., vol. 52, Fasc. 8 (1969).
Matsui et al., Chem. Abst. 78-97477g (1973).
Jeanmart et al., Chem. Abst. 87-184560h (1977).

Primary Examiner—Cecilia Shen
Attorney, Agent, or Firm—Wegner & Bretschneider

[57] ABSTRACT

The compound of the formula

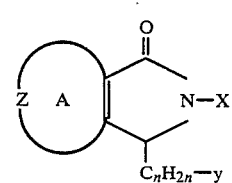

wherein X is a cyclic group which may optionally be substituted; Y is a carboxyl group which may optionally be esterified or amidated; Z is $-CH=CH-CH=CH-$, $-S-(CH_2)_l-S-$ is an integer of 1 to 3), $-N=CH-CH=N-$ or $-(CH_2)_m-$ (m is an integer of 3 to 5); ring A may optionally be substituted with halogen, nitro, amino, alkanoylamino, alkoxycarbonyl, carboxyl or carbamoyl; and n is an integer of 1 to 3, and salts thereof. The compounds display a strong antianxiety effect to mammalian animals and are useful for the prevention or treatment of a disease such as psychoromatic disease and anxiety neurosis.

8 Claims, No Drawings

PYRROLS [3,4-b]PYRAZINE DERIVATIVES, THEIR PRODUCTION AND USE AS ANTI-ANXIETY AGENTS

This application is a divisional of application Ser. No. 832,138, now allowed, which is a divisional of Ser. No. 478,478, filed Mar. 24, 1983, now U.S. Pat. No. 4,590,189, issued May 20, 1986.

This invention relates to novel condensed pyrrolinone derivatives of value as medicines their production and use.

Heretofore benzodiazepine compounds have been broadly employed as antianxiety drug but, because of the drug dependence and side effects such as hypnotic and muscle relaxing effets they produce are not fully satisfactory. The present inventors conducted a series of researches to develop antianxiety drugs in the non-benzodiazepine series and succeeded in the production of compounds having very satisfactory properties. This invention has come forth from the above finding and successful production.

The invention provides compounds of the formula

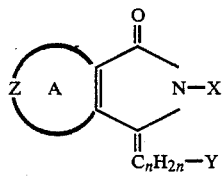
(I)

wherein
X is a cyclic group which may optionally be substituted;
Y is a carbonyl group which may optionally be esterified or amidated; Z is —CH=CH—CH=CH—, —S—(CH$_2$)$_l$—S— (l is an integer of 1 to 3), —N=CH—CH=N—, or —(CH$_2$)$_m$— (m is an integer of 3 to 5); ring A may optionally be substituted by halogen, nitro, amino, alkanoylamino, alkoxycarbonyl, carboxyl or carbamoyl; and n is an integer of 1 to 3, and salts thereof.

Referring to the above formula (I), ring A may optionally be substituted by one or 2 substituents just mentioned above. Referring to the substituent, halogen includes chlorine, bromine, fluorine and iodine, preferably chlorine; alkanoylamino includes C$_{2-5}$ alkanoylamino (e.g. acetylamino, propionylamino, butyrylamino, etc.); alkoxycarbonyl includes C$_{2-5}$ alkoxycarbonyl (e.g. methoxycarbonyl, ethoxycarbonyl, propoxycarbonyl, etc.). These substituents may be on any position of the ring A. When Z is —CH=CH—CH=CH—, the substituent(s) preferably be at 5- and/or 6-position of the ring as isoindolinone. When Z is —(CH$_2$)$_m$—, m is preferably 4. Z is preferably —CH=CH—CH=CH— or —S—(CH$_2$)$_l$—S— (l is preferably 1 or 2).

The cyclic group X may for example be an aryl (e.g. phenyl, naphthyl), aromatic heterocycle (e.g. pyridyl, pyridazinyl, pyrazinyl, pyrimidinyl, quinolyl, naphthyridinyl, thiazolyl, benzothiazolyl) or C$_{3-7}$ cycloalkyl (e.g. cyclopentyl, cyclohexyl, cycloheptyl), especially phenyl and naphthyridinyl being preferable. Such cyclic group may optionally have 1 to 3 substituents, for example halogen (e.g. Cl, Br, F, I), C$_{1-4}$ alkyl (e.g. methyl, ethyl, propyl, butyl, isobutyl), C$_{1-4}$ alkoxy (e.g. methoxy, ethoxy, propoxy, isopropoxy), methylenedioxy, phenoxy, benzyloxy, hydroxy, C$_{2-5}$ alkanoyloxy (e.g. acetoxy, propionyloxy, butyryloxy), amino, di-C$_{1-4}$ alkylamino (e.g. dimethylamino, diethylamino, dipropylamino, dibutylamino), ω-hydroxy-C$_{1-3}$ alkyl (e.g. hydroxymethyl, hydroxyethyl), C$_{2-5}$ alkanoyl (e.g. acetyl, propionyl, butyryl), benzoyl, amido, nitro, cyano, trifluoromethyl, C$_{1-4}$ alkylthio (e.g. methylthio, ethylthio, propylthio, butylthio), C$_{2-5}$ alkanoyloxy-C$_{1-3}$ alkyl (e.g. acetyloxyethyl, propionyloxymethyl), C$_{2-5}$ alkanoylamino (e.g. acetylamino, propionylamino), or alkoxycarbonyl (e.g. methoxycarbonyl, ethoxycarbonyl).

The above-mentioned cyclic group is preferably unsubstituted or substituted with one halogen atom or C$_{1-4}$ alkoxy group.

The carboxyl group Y may optionally be esterified or amidated. The esterified carboxyl group is represented by the formula

(a)

and the amidated carboxyl group is represented by the formula

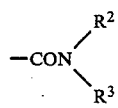
(b)

Referring to formula (a), R$^1$ may for example be an C$_{1-4}$ alkyl group (e.g. methyl, ethyl, propyl, isopropyl, butyl, isobutyl, tert-butyl), a phenyl-C$_{1-4}$ alkyl group (e.g. benzyl) or a phenyl group.

In formula (b), R$^2$ and R$^3$ are the same or different and each may for example be hydrogen, a C$_{1-4}$ alkyl group (e.g. methyl, ethyl, propyl, isopropyl), a phenyl-C$_{1-4}$ alkyl (e.g. benzyl, phenethyl, α-methylbenzyl), a phenyl group, a thiazolyl group or a benzothiazolyl group, and these groups may each have such substituents as for example, halogen (e.g. Cl, Br, F, I), hydroxy, C$_{1-4}$ alkoxy (e.g. methoxy, ethoxy, propoxy, isopropoxy), C$_{2-5}$ alkoxycarbonyl (e.g. methoxycarbonyl, ethoxycarbonyl) and di-C$_{1-4}$ alkylamino (e.g. dimethylamino, diethylamino).

Moreover, R$^2$ and R$^3$ may, together with the adjacent N atom, form a cyclic amino group which is usually a 5- to 7-membered cyclic amino which may include N, O or S as a second hetero-atom, in addition to the above N atom. Examples of such cyclic amino group is 5- to 7-membered heterocycle having one N atom such as pyrrolidinyl, piperidino and hexahydroazepinyl or 5- to 7-membered heterocycle having two N atoms, one N and one S atoms, or one N and one O atoms such as piperazinyl, morpholino and thiazolidinyl, etc. Each of these cyclic amino groups may have 1 to 2 substituents which may for example be hydroxy, C$_{1-4}$ alkoxy (e.g. methoxy, ethoxy, propoxy, isopropoxy), C$_{1-4}$ alkyl (e.g. methyl, ethyl, propyl, isopropyl), C$_{2-5}$ alkoxycarbonyl (e.g. methoxycarbonyl, ethoxycarbonyl), phenyl-C$_{1-4}$ alkyl (e.g. benzyl, phenethyl, α-methylbenzyl), phenyl, piperidino, pyridyl, etc. Among these substituents, cyclic groups (e.g. phenyl) may further have substituents as halogen, hydroxy, C$_{1-4}$ alkyl, C$_{1-4}$ alkoxy, trifluoromethyl, etc.

The saturated hydrocarbon group C$_n$H$_{2n}$ may be either a straight-chain group or a branched-chain group, and is preferably a group in which n is 1 or 2, especially 1.

The compound (I) of this invention can be produced, for example by hydrolyzing a compound of the formula

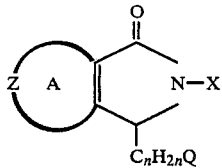

(II)

wherein each symbol is as defined hereinbefore; Q is —COOR⁴ (R⁴ is a lower alkyl group) or —CN, and, if necessary, esterifying or amidating the hydrolysate compound.

More specifically, (1) the compound (I) wherein Y is a carboxyl group, i.e. one having the formula

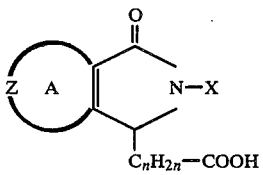

(I-1)

wherein each symbol is as defined hereinbefore, can be produced by the following reactions:

where n=1

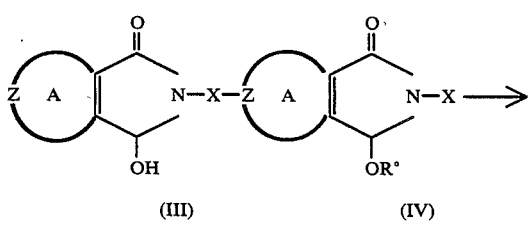

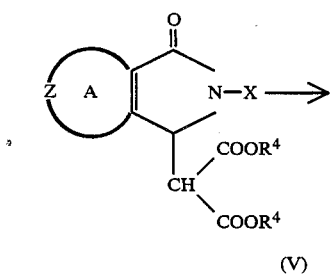

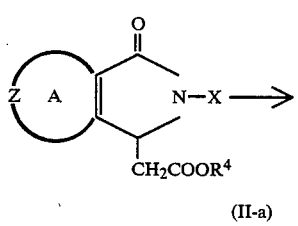

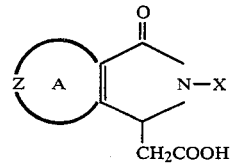

(I-1)

In the above reaction formulas each symbol is as defined hereinbefore; R⁰ is a lower alkyl group.

The starting compound of general formula (III) can be produced in accordance with the process described in J. Org. Chem. 26, 2273 (1961) or by the process described in J. Org. Chem. 26, 2273 (1961) from a compound of general formula (III') which can be prepared by or in general accordance with the processes described in Japanese patent publication No. 11940/1973, Japanese published and unexamined Pat. No. 100495/1977 (Kokai Sho-52-100495), Helv. Chim. Acta 52, 2228 (1965), J. Hetelocycl. Chem. 7, 1121 (1970), and Chem. Ber. 40, 4850 (1907).

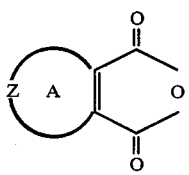

(III')

wherein each symbol is as defined hereinbefore.

Thus, a compound of general formula (III) is dissolved in a lower alkanol (R⁰OH) and the solution is heated together with a catalyst amount of concentrated hydrochloric acid, whereby the alkyl ether (IV) is easily obtained. The ether compound (IV) can be easily converted to a compound (V) by the reaction of (IV) with a malonic acid diester (e.g. dimethyl malonate, diethyl malonate) under the ordinary conditions of Friedel-Crafts reaction, for example in dichloromethane or dichloroethane solvent in the presence of aluminum chloride. When the compound (V) is heated at 170° to 180° C. in dimethyl sulfoxide in the presence of a slight excess of sodium chloride and water, there is produced (II-a). This (II-a) is then hydrolyzed in the presence of a base such as potassium carbonate, sodium hydroxide or potassium hydroxide to give the compound (I-1). This reaction is generally conducted in a solvent such as methanol, ethanol, tetrahydrofuran, dimethylformamide, etc. The reaction is conducted at a temperature of −10° C. to +100° C. and generally at a temperature between room temperature and the boiling point of the solvent (e.g. methanol):

where n=2

In this case, a compound of general formula (V) is reacted in the following steps to give the compound (I-1) wherein n is 2.

(V) → 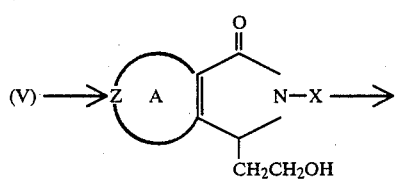

(VI)

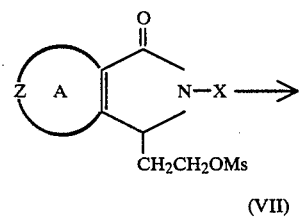

(VII)

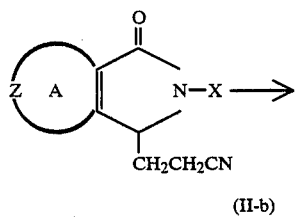

(II-b)

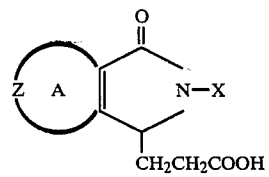

(I-1)

In the above reaction formulas, Ms is a methanesulfonyl group; each of the other symbols is as defined hereinbefore.

Thus, reduction of (V) with lithium borohydride, for instance, gives rise to a compound of general formula (VI). This reaction is conducted in tetrahydrofuran and generally at room temperature, although the reaction rate may be adjusted by cooling or heating, if necessary. The (VI) is reacted with methanesulfonyl chloride in pyridine to give a mesylate (VII) which is then reacted with potassium cyanide to give a compound of general formula (II-b). This reaction is carried out by refluxing in aqueous methanol or aqueous ethanol, for instance. The resulting compound (II-b) is hydrolyzed to a compound (I-1) wherein n is 2. This hydrolysis reaction can be effected by the conventional process for hydrolysis of a nitrile group, for example by hydrolyzing in protic solvents (e.g. water, methanol, ethanol, DMF, DMSO, etc.) in the presence of acids (e.g. HCl, $H_2SO_4$, $H_3PO_4$, etc.) or bases (e.g. NaOH, KOH, LiOH, etc.) for 30 minutes to 20 hours:

where n=3

In this case, a compound of general formula (VII) is reacted in the following steps to give the compound (I-1) wherein n is 3.

(VII) → 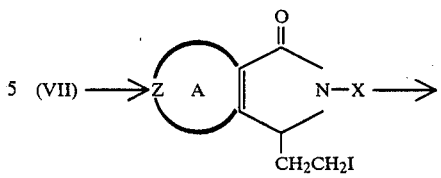

(VIII)

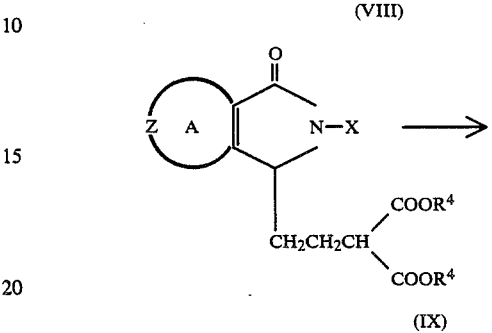

(IX)

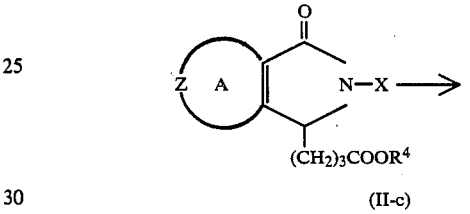

(II-c)

(I-1)

In the reaction formulas, each symbol is as defined hereinbefore.

Thus, a compound of general formula (VII) is reacted with sodium iodide at an elevated temperature in an organic solvent such as acetone, dimethylformamide, tetrahydrofuran, etc. to give an iodide derivative (VIII) which, in turn, is reacted with a malonic acid diester (e.g. dimethyl malonate, diethyl malonate) to give a compound of general formula (IX). Then, in the same manner as the production of (I-1) from (VI), (IX) is first converted to (II-c) which is then hydrolyzed to a compound (I-1) wherein n is 3 in a conventional manner as described before.

(2) The compound (I) wherein Y is an esterified carboxyl group, i.e. a compound of formula

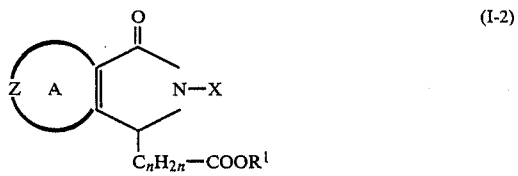

(I-2)

wherein $R^1$ is as defined hereinbefore can be produced by esterifying the carboxylic acid (I-1) obtained in (1) described above or a reactive derivative thereof with an alcohol of the formula $R^1OH$ (X)

wherein $R^1$ is as defined hereinbefore.

In the reaction of carboxylic acid (I-1) with alcohol (X), a mixture thereof is heated in the presence of a catalyst to give an ester (I-2). This reaction is generally effected using an excess of alcohol (X) and can be hastened by azeotropic removal of water formed during the reaction. The catalyst may be an inorganic acid such as sulfuric acid, hydrochloric acid, etc. an organic acid or an anhydride thereof such as paratoluenesulfonic acid, trifluoroacetic anhydride, trifluoromethanesulfonic anhydride, etc., or a salt of a heavy metal as tin, cobalt, iron, aluminum etc. (e.g. $BuSnO_2H$, $Bu_2SnO$). An alternative process in which (I-1) is reacted with alcohol (X) to give (I-2) is a reaction in the presence of a dehydrating agent such as dicyclohexylcarbodiimide, carbonyldiimidazole, etc. This reaction is generally conducted in pyridine, but any other organic solvent that will not interfere with the reaction can be equally employed. The reaction temperature may range from about $-20°$ C. to about $+150°$ C. and, generally, the reaction proceeds satisfactorily at room temperature.

As examples of said reactive derivative of (I-1) there may be mentioned the acid halides (e.g. acid chloride, acid bromide), the acid anhydride obtainable by elimination of one molecule of water from 2 molecules of (I-1), and the mixed acid anhydrides obtainable by replacing the carboxyl hydrogen of (I-1) with ethoxycarbonyl, isobutyloxycarbonyl, benzyloxycarbonyl, etc. The reaction of such a reactive derivative with alcohol (X) can be generally conducted in a solvent that does not interfere with the reaction, such as ether, benzene, tetrahydrofuran, dichloromethane, chloroform, dimethylformamide, etc. When necessary, this reaction is conducted in the presence of a base such as pyridine, triethylamine, 4-dimethylaminopyridine, diisopropylethylamine, triethylenediamine, etc. and the reaction temperature is about $-10°$ to $+100°$ C. and, preferably, $0°$ to $30°$ C.

The compound (I-2) can also be produced by reacting an alkali metal salt (e.g. sodium salt) or silver salt of (I-1) with a halide of formula $R^1-B$ (XI)

wherein $R^1$ is as defined hereinbefore; B is a halogen atom.

The compound (I-2) wherein $R^1$ is a tert-butyl group can also be produced by adding (I-1) to isobutylene. This reaction is conducted in the presence of an acid catalyst such as sulfuric acid, boron trifluoride, etc.

Furthermore, in the process of synthesis of (II-a) from compound (IV), by using a di-lower alkyl ester of malonic acid or other various ester, there can be produced the corresponding ester (I-2). (3) The compound (I) wherein Y is an amidated carboxyl group i.e. a compound of formula

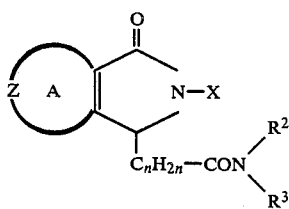 (I-3)

wherein each symbol is as defined hereinbefore can be produced by reacting an ester (I-2) or a carboxylic acid (I-1) obtained in (1) or a reactive derivative thereof with an amino compound of formula

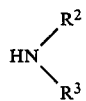 (XII)

wherein each symbol is as defined hereinbefore.

For producing the compound (I-3) by reacting the ester (I-2) with the amino compound (XII), the reaction is carried out either in a solvent such as toluene, exylene, dichloromethane, chloroform, ethyl acetate, tetrahydrofuran, dimethylformamide, etc. or in no solvent. As necessary, the reaction may be conducted in the presence of a base such as pyridine, picoline, triethylamine, 4-dimethylaminopyridine, potassium carbonate, sodium carbonate, etc., an acid such as p-toluenesulfonic acid, methanesulfonic acid, trifluoroacetic acid, etc. or an alkali metal salt such as lithium chloride, sodium chloride, sodium iodide, lithium iodide, lithium bromide, soidum bromide, etc. The reaction to normally carried out at a temperature of $0°-260°$ C., and preferably $60°$ to $130°$ C.

The reactive derivative of the carboxyl group of said compound (I-1) includes, in addition to those employed in the above-mentioned process (2), such other derivatives as N-hydroxydiacylimide esters (e.g. N-hydroxysuccinimide ester, N-hydroxyphthalimide ester, N-hydroxy-5-norbornene-2,3-dicarboximide ester), for instance. This reaction is generally conducted in a solvent such as dichloromethane, tetrahydrofuran, chloroform, dimethylformamide, acetonitrile, etc. These solvents are mentioned only as examples and any other solvent that does not interfere with the reaction can be successfully employed. If necessary, this reaction can be conducted in the presence of a base such as pyridine, triethylamine, 4-dimethylaminopyridine, diisopropylethylmaine, triethylenediamine, potassium carbonate, sodium hydroxide, etc. The reaction temperature is generally about $-10°$ C. to about $+100°$ C., and preferably $0°$ C. to $30°$ C. When (I-1) as such, instead of a reactive derivative thereof, is employed, the reaction is conducted in the presence of a dehydrating agent such as a dicyclohexylcarbodiimide, carbonyldiimidazole, diethyl phosphorocyanidate, diphenylphosphoryl azide, etc. The reaction may also be conducted in the presence of a base such as pyridine, picoline, triethylamine, sodium hydroxide, potassium carbonate, etc. The reaction is generally conducted at a temperature of about $-20°$ C. to about $+150°$ C. In most instances, the reaction proceeds satisfactorily at room temperature.

Moreover, the compound (I) wherein n is 1 can also be produced in one step by reacting said compound (III) with a compound of formula $Ph_3P=CHY$ (XIII)

wherein Y is as defined hereinbefore.

This reaction is conducted in an organic solvent such as toluene, ethyl acetate, methoxyethane, or the like. Aside from these solvents, any other organic solvent that does not interfere with the reaction can also be employed. The reaction temperature is generally about $10°$ C. to $120°$ C. When Y is an esterified carboxyl group (I-2, n=1), the amide (I-3) can be produced by the treatment of the ester (I-2, n=1) with the amine (XII) described above under the noted reaction conditions. If necessary, it is first hydrolyzed to the free carboxyl group. It is then converted to a reactive derivative such as an acid chloride or a mixed acid anhydride and reacted with the amine mentioned above. Or the above carboxylic acid is reacted with the amine in the presence of an acid activator such as carbonylimidazole or diethyl phosphorocyanidate to give a compound (I-3, n=1) wherein Y is an amidated carboxyl group.

Among the above-mentioned compounds (XIII), the compound of formula

$$Ph_3P=CHCOOR^1 \quad (XIII\text{-}2)$$

wherein $R^1$ is as defined hereinbefore, is a known compound and can be prepared for example by the process described in Helv. Chim. Acta. 44, 1242 (1957).

The compound of formula

$$Ph_3P=CHCON\begin{matrix}R^2\\R^3\end{matrix} \quad (XIII\text{-}3)$$

wherein $R^2$ and $R^3$ are as defined hereinbefore, is a novel compound and can be produced for example by the steps of treating an α-haloacetamide compound of formula

$$B'CH_2CON\begin{matrix}R^2\\R^3\end{matrix} \quad (XIV)$$

wherein B' is a halogen atom; and $R^2$ and $R^3$ are as defined hereinbefore and triphenylphosphine in the known manner, for example by heating them together at 10° to 120° C. in toluene, benzene, ethyl acetate, acetonitrile, dimethylformamide or the like and treating the resulting phosphonium salt

$$Ph_3P^{\oplus}-CH_2CON\begin{matrix}R^2\\R^3\end{matrix} \; B'^{\ominus} \quad (XV)$$

wherein B', $R^2$ and $R^3$ are as defined hereinbefore in the known manner, for example by reacting (XV) with an alkali, e.g. sodium hydroxide or potassium hydroxide, in aqueous solution at 0° to 50° C.

This compound (XIII-3) is not only useful as an intermediate for the production of compound (I, n=1) according to this invention but also can be reacted with various aldehydes or ketones to give the corresponding methylenecarboxamides, thus being of value as intermediates for the synthesis of a variety of compounds.

The compounds (I) of this invention which can be produced by the above-described reactions, i.e. compounds (I-1), (I-2) and (I-3), can each be isolated from the reaction mixture by separation and purification procedures known per se (e.g. extraction, recrystallization, column chromatography).

The compound (I-1) wherein Y is a free carboxyl group can be isolated in the form of a salt, for example as a metal salt such as the sodium, potassium or calcium salt. When the compound (I) of this invention is basic, it can be isolated in the form of a salt with an acid, examples of which are pharmaceutically acceptable salts such as salts with inorganic acids (e.g. hydrochloride, nitrate, phosphate, hydrobromide) or salts with organic acids (e.g. acetate, fumarate, maleate, oxalate, tartarate, methanesulfonate, etc.).

There are optical isomers for compounds of this invention and such isomers as well as racemes are also within the scope of this invention. In each of the above-mentioned processes, (I) is generally produced in racemic form but can be resolved into two optically active compounds by the conventional optical resolution procedure, if desired.

The compound (I) according to the invention, particularly the compound (I-3), acts on the central nervous system to display a strong antianxiety effect as demonstrated by anticonflict tests in rats. The minimal lethal dose (MLD) of the compound of this invention is at least 500 mg/kg in mice and the minimal effective dose (MED) is not more than 2.5 mg/kg in rats. Since the safety margin of the compound is very large and its hypnotic and muscle relaxing effects as side effects are very weak as compared with the benzodiazepine antianxiety drugs currently on the market, it can be administered safely and effectively as an antianxiety drug to mammalian animals including human beings. The indications of this compound may include various psychosomatic diseases such as autonomic invalance, nervous vomiting, neurodermatitis, alopecia areata, nervous angina, nervous dyspnea, etc. as well as anxiety neurosis, and the compound (I) can be used for the prevention or treatment of such diseases. Furthermore, this compound has anticonvulsant activity and, therefore, can be used in cases of epilepsy, traumatic convulsion, etc. The compound according to this invention can be administered orally or otherwise to mammalian animals including man, in various dosage forms such as tablets, granules, capsules, injections, suppositories, etc. While the dosage depends on the disease, condition, etc., the compound is administered generally in the daily dose of about 0.001 to 50 mg per kg body weight in the case of animals and in the daily dose of 0.1 to 100 mg, or preferably 0.5 to 20 mg, in the case of an adult human.

Furthermore, as is apparent from the foregoing description of production processes, the compounds (I-1) and (I-2) according to this invention are of use as intermediates for the production of (I-3).

The reference and working examples of this invention set forth hereinafter are further illustrative of this invention but should by no means be construed as limiting its scope.

Test Example

The pharmacological properties of the compounds (I) of this invention were investigated by determining the substituting power thereof for radioactive diazepam from a benzodiazepine receptor.

(Method)

Specific benzodiazepine receptor binding was carried out according to the method of C. Braestrup and R. F. Squiras (European J. Pharmacol., Vol. 48, 263–270, 1978). Thus, crude mitochondrial fractions obtained from the cerebral cortex of male SD strain rats 9 to 10 weeks of age were suspended in 50 mM Tris-HCl buffer (pH 7.4) and incubated with one of a series of concentrations of the test compound and ($^3$H) diazepam (final concentration 2 nM) at 4° C. for 20 minutes. Then, the suspension was filtered through a Whatman GF/B glass fiber filter and the radioactivity of ($^3$H) diazepam on the filter was measured by the liquid scintilation method. The concentration of the test drug which caused a 50% inhibition of ($^3$H) diazepam specific binding was taken as the IC$_{50}$ value.

(Test Result)

TABLE 1

Effect on specific binding of [$^3$H] diazepam

| Compound (I) A ring | X | n | Y | IC$_{50}$ [nM] |
|---|---|---|---|---|
| benzene | 4-Cl-phenyl | 1 | CON(piperidine) | 8.86 |
| benzene | phenyl | 1 | CON(CH$_3$)CH$_2$-phenyl | 19.50 |
| 4-Cl-benzene | 4-OCH$_3$-phenyl | 1 | CON(N-CH$_3$ piperazine) | 1.99 |
| 4-Cl-benzene | 4-OCH$_3$-phenyl | 1 | CON(piperidine) | 0.794 |
| benzene | 4-OCH$_3$-phenyl | 1 | CON(piperidine) | 4.46 |
| 4-O$_2$N-benzene | 4-OCH$_3$-phenyl | 1 | CON(piperidine) | 2.40 |
| benzene | 2-N, 8-N, 7-Cl-naphthyridine | 1 | CON(piperidine) | 0.645 |
| 4-H$_2$N-benzene | 4-OCH$_3$-phenyl | 1 | CON(piperidine) | 3.80 |
| benzene | 4-OCH$_3$-phenyl | 1 | CON(thiazolidine) | 4.90 |
| 1,3-dithiolane | 4-Cl-phenyl | 1 | CON(piperidine) | 9.55 |
| 1,3-dithiolane | 4-Cl-phenyl | 1 | CON(azepane) | 5.75 |
| 1,3-dithiolane | 4-OCH$_3$-phenyl | 1 | CON(piperidine) | 1.05 |

TABLE 1-continued

Effect on specific binding of [$^3$H] diazepam

| Compound (I) | | | | IC$_{50}$ |
|---|---|---|---|---|
| A ring | X | n | Y | [nM] |
| 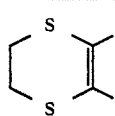 | 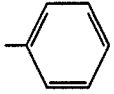 | 1 | CON | 7.58 |

EXAMPLE 1

3-Oxo-2-phenylisoindoline-1-acetic acid (a) Concentrated hydrochloric acid (1 ml) was added to a solution of 27 g of 3-hydroxy-2-phenylisoindolin-1-one in 300 ml of methanol and the mixture was refluxed for 1.5 hours. Then, 200 ml of the methanol was distilled off under reduced pressure and 500 ml of a saturated sodium hydrogen carbonate solution was added, followed by extraction with ethyl acetate. The extract was washed with water and dried, and the solvent was distilled off to give 28 g of crystals of 3-methoxy-2-phenylisoindolin-1-one, which, after recrystallization from ethyl acetate, melted at 83°–84° C.

Elemental analysis: Calcd. for C$_{15}$H$_{13}$NO$_2$: C, 75.30: H, 5.48: N, 5.85, Found: C, 75.57: H, 5.33: N, 5.93.

(b) A solution of 8.3 g of the above product and 6.7 g of diethyl malonate in 50 ml of dichloroethane was added dropwise to a suspension of 7.5 g of aluminum chloride in 80 ml of dichloroethane with stirring at room temperature. After completion of addition, the mixture was refluxed for 40 minutes and then cooled. Then, 300 ml of 6N hydrochloric acid was added and the mixture was stirred at room temperature for an hour, followed by addition of 150 ml of dichloroethane. The resulting mixture was shaken well and the organic layer was separated, washed with water, aqueous sodium hydrogen carbonate and water in that order, and dried. The solvent was then distilled off to give 10.5 g of ethyl 3-oxo-2-phenylisoindoline-1-malonate as an oil.

(c) The above product (10.5 g) was dissolved in 20 ml of dimethyl sulfoxide, to the solution 0.51 g of water and 1.7 g of sodium chloride were added, and the mixture was stirred with heating at 170° C.–180° C. for 3 hours. After cooling, the reaction mixture was poured into 500 ml of ice water and extracted with 400 ml of a 1:1 ethyl acetate-ether mixture. After washing and dehydration, the solvent was distilled off. The crystalline residue was washed with hexane and collected by filtration to give 5.6 g of ethyl-3-oxo-2-phenylisoindoline-1-acetate, which was purified by recrystallization from ether, melted at 109° C.–110° C.

Elemental analysis: Calcd. for C$_{18}$H$_{17}$NO$_3$: C, 73.20: H, 5.80: N, 4.74, Found: C, 72.89: H, 5.61: N, 4.79.

(d) The above crystals (5 g) were dissolved in 50 ml of methanol, to the solution 15 ml of a 15% aqueous solution of potassium carbonate was added, and the mixture was refluxed for 1.5 hours. The methanol was distilled off under reduced pressure, followed by addition of 100 ml of water and 100 ml of ether. The mixture was shaken, and the aqueous layer was separated and acidified with concentrated hydrochloric acid. The crystalline precipitate was collected by filtration and dried. Recrystallization from methanol-ethyl acetate gave the title compound melting at 204°–205° C. Yield: 3.8 g.

Elemental analysis: Calcd. for C$_{16}$H$_{13}$NO$_3$: C, 71.90: H, 4.90: N, 5.24, Found: C, 72.07: H, 5.00: N, 5.30.

EXAMPLE 2

The following 3-oxo-2-(substituted-phenyl)isoindoline-1-acetic acids were produced from the corresponding 3-hydroxy-2-(substituted-phenyl)isoindolin-1-ones in a manner similar to that of Example 1:

(i) 3-Oxo-2-(2-chlorophenyl)isoindoline-1-acetic acid
M.p. 163°–165° C.
Elemental analysis: Calcd. for C$_{16}$H$_{12}$NO$_3$Cl: C, 63.82: H, 4.00: N, 4.64, Found: C, 63.79: H, 4.12: N, 4.77.

(ii) 3-Oxo-2-(3-chlorophenyl)isoindoline-1-acetic acid
M.p. 157°–160° C.
Elemental analysis: Calcd. for C$_{16}$H$_{12}$NO$_3$Cl: C, 63.69: H, 4.00: N, 4.64, Found: C, 63.82: H, 4.04: N, 4.46.

(iii) 3-Oxo-2-(4-chlorophenyl)isoindoline-1-acetic acid
M.P. 204°–205° C.
Elemental analysis: Calcd. for C$_{16}$H$_{12}$NO$_3$Cl: C, 63.69: H, 4.00: N, 4.64, Found: C, 63.74: H, 3.97: N, 4.16.

(iv) 3-Oxo-2-(4-methoxyphenyl)isoindoline-1-acetic acid
M.P. 222°–223° C.
Elemental analysis: Calcd. for C$_{17}$H$_{15}$NO$_4$: C, 68.67: H, 5.08: N, 4.71, Found: C, 68.49: H, 4.90: N, 4.69.

(v) 3-Oxo-2-(5-chloro-2-pyridyl)isoindoline-1-acetic acid
M.P. 159°–160° C.
Elemental analysis: Calcd. for C$_{15}$H$_{11}$N$_2$O$_3$Cl: C, 59.51: H, 3.66: N, 9.25, Found: C, 59.76: H, 3.66: N, 9.11.

EXAMPLE 3

2-Phenyl-3-piperidinocarbonylmethylisoindolin-1-one

A mixture of 1.8 g of 3-oxo-2-phenylisoindoline-1-acetic acid and 7 ml of thionyl chloride was heated at 70° C. for 10 minutes and the excess thionyl chloride was distilled off under reduced pressure to give the corresponding acid chloride. Triethylamine (1 ml) was added to a solution of 0.62 g of piperidine in 30 ml of methylene chloride and to this solution the above-mentioned acid chloride was added portionwise with stirring at room temperature. The mixture was further stirred at room temperature for 30 minutes, 100 ml of methylene chloride was added, and the whole mixture was washed with water. After drying, the solvent was distilled off to give 1.8 g of crystals, which were recrystallized from ethyl acetate.

M.p. 122°–123° C., 134°–136° C. (double-melting point).

Elemental analysis: Calcd. for C$_{21}$H$_{22}$N$_2$O$_2$: C, 75.42: H, 6.63: N, 8.38, Found: C, 75.42: H, 6.44: N, 8.25.

EXAMPLE 4

In the same manner as Example 3, there were obtained the compounds listed in Table 2.

TABLE 2

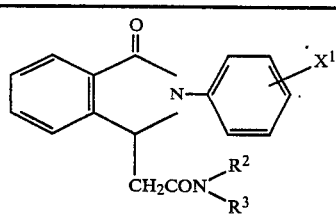

| No. | $X^1$ | $N\begin{smallmatrix}R^2\\R^3\end{smallmatrix}$ | M.p. [°C.] | molecular formula | Elemental analysis Calcd. (Found) C | H | N |
|---|---|---|---|---|---|---|---|
| 1 | H | $N(C_2H_5)_2$ | 89~90 | $C_{20}H_{22}N_2O_2$ | 74.51 (74.45) | 6.88 (6.94) | 8.69 (8.78) |
| 2 | H | $N(CH_3)(CH_2Ph)$ | 110~118 | $C_{24}H_{22}N_2O_2$ | 77.81 (77.95) | 5.99 (6.00) | 7.56 (7.34) |
| 3 | H | pyrrolidine | 199~200 | $C_{20}H_{20}N_2O_2$ | 74.97 (74.79) | 6.29 (6.02) | 8.74 (8.64) |
| 4 | H | piperidine | 122~123 <br> 134~136 } * | $C_{21}H_{22}N_2O_2$ | 75.42 (75.42) | 6.63 (6.44) | 8.38 (8.25) |
| 5 | H | hexamethyleneimine | 134~135 | $C_{22}H_{24}N_2O_2$ | 75.83 (75.93) | 6.94 (6.67) | 8.04 (7.96) |
| 6 | H | 4-(ethoxycarbonyl)piperidine | 104~105 | $C_{24}H_{26}N_2O_4$ | 70.91 (71.03) | 6.45 (6.55) | 6.89 (6.99) |
| 7 | H | 4-hydroxy-4-phenylpiperidine | 221~223 | $C_{27}H_{26}N_2O_3$ | 76.03 (75.71) | 6.15 (6.18) | 6.57 (6.27) |
| 8 | H | 4-piperidinopiperidine | 145~148 | $C_{26}H_{31}N_3O_2$ | 74.79 (74.94) | 7.48 (7.33) | 10.06 (10.04) |
| 9 | H | 4-phenylpiperidine | 200~201 | $C_{27}H_{26}N_2O_2$ | 79.00 (79.01) | 6.38 (6.39) | 6.83 (6.74) |
| 10 | H | 4-methylpiperazine | 136~161 | $C_{21}H_{23}N_3O_2$ | 72.18 (72.17) | 6.63 (6.55) | 12.03 (11.82) |
| 11 | H | piperazine·HCl·½C$_2$H$_5$OH | 238~244 | $C_{21}H_{21}N_3O_2$·HCl·½$C_2H_6O$ | 63.87 (63.78) | 6.38 (6.03) | 10.64 (10.93) |

TABLE 2-continued
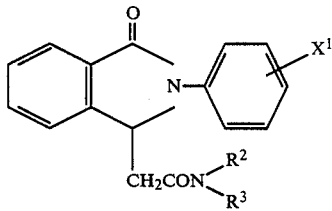
| No. | X¹ | $\mathrm{HN}\begin{smallmatrix}R^2\\R^3\end{smallmatrix}$ | M.p. [°C.] | molecular formula | Elemental analysis Calcd. (Found) | | |
|---|---|---|---|---|---|---|---|
| | | | | | C | H | N |
| 12 | H | 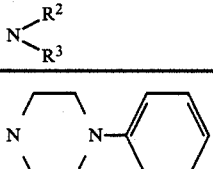 | 168~190 | $C_{26}H_{25}N_3O_2$ | 75.89 (75.82) | 6.12 (6.29) | 10.21 (9.94) |
| 13 | H | 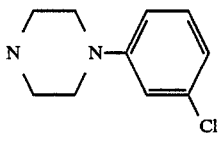 | 166~180 | $C_{26}H_{24}ClN_3O_2$ | 70.02 (70.04) | 5.43 (5.32) | 9.42 (9.34) |
| 14 | H | 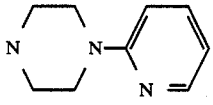 | 192~206 | $C_{25}H_{24}N_4O_2$ | 72.79 (72.63) | 5.87 (6.10) | 13.58 (13.50) |
| 15 | H | 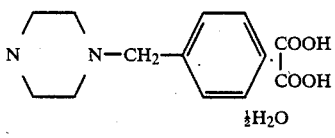 | 207~210 | $C_{27}H_{27}N_3O_2 \cdot C_2H_2O_4 \cdot \tfrac{1}{2}H_2O$ | 66.40 (66.26) | 5.76 (5.63) | 8.01 (8.17) |
| 16 | H | 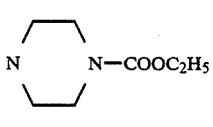 | 85~93 | $C_{23}H_{25}N_3O_4$ | 67.79 (68.00) | 6.18 (6.08) | 10.31 (10.22) |
| 17 | H | 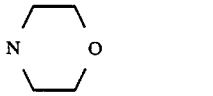 | 144~146 | $C_{20}H_{20}N_2O_3$ | 71.41 (71.49) | 5.99 (5.83) | 8.33 (7.95) |
| 18 | H | 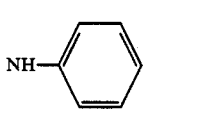 | 177~178 | $C_{22}H_{18}N_2O_2$ | 77.17 (77.40) | 5.30 (5.37) | 8.18 (8.22) |
| 19 | H | NHCH₂COOC₂H₅ | 139~140 | $C_{20}H_{20}N_2O_4$ | 68.17 (67.85) | 5.72 (6.12) | 7.95 (7.77) |
| 20 | H | 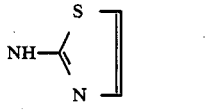 | 247~248 | $C_{19}H_{15}N_3O_2S$ | 65.31 (65.39) | 4.33 (4.21) | 12.03 (11.96) |
| 21 | H | 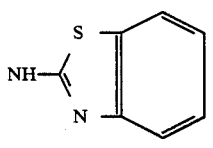 | 265.5~267.5 | $C_{23}H_{17}N_3O_2S$ | 69.15 (69.32) | 4.29 (4.24) | 10.52 (10.46) |
| 22 | H | 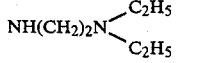 | oil | $C_{22}H_{27}N_3O_2$ | 72.30 (70.51) | 7.45 (7.49) | 11.50 (11.32) |

TABLE 2-continued

[Structure: 2-substituted benzamide with CH2CON(R2)(R3) side chain and N-aryl group bearing X1]

| No. | X¹ | NR²R³ | M.p. [°C.] | molecular formula | Elemental analysis Calcd. (Found) C | H | N |
|---|---|---|---|---|---|---|---|
| 23 | o-Cl | piperidino | 139~140 | $C_{21}H_{21}N_2O_2Cl$ | 68.38 (68.41) | 5.73 (5.57) | 7.59 (7.38) |
| 24 | o-Cl | 4-methylpiperazino | 132~134 | $C_{21}H_{22}N_3O_2Cl$ | 65.70 (65.57) | 5.77 (5.76) | 10.95 (10.61) |
| 25 | m-Cl | piperidino | 123~124 | $C_{21}H_{21}N_2O_2Cl$ | 68.38 (68.13) | 5.73 (5.53) | 7.59 (7.34) |
| 26 | m-Cl | 4-methylpiperazino | 126~127 | $C_{21}H_{22}N_3O_2Cl$ | 65.70 (65.80) | 5.77 (5.60) | 10.95 (10.89) |
| 27 | p-Cl | piperidino | 128~129 | $C_{21}H_{21}N_2O_2Cl$ | 68.38 (68.53) | 5.73 (5.76) | 7.59 (7.42) |
| 28 | p-Cl | 4-methylpiperazino | 154~155 | $C_{21}H_{22}N_3O_2Cl$ | 65.70 (65.47) | 5.77 (5.79) | 10.95 (10.60) |
| 29 | p-OCH₃ | piperidino | 86~88 | $C_{22}H_{24}N_2O_3$ | 72.50 (72.54) | 6.64 (6.79) | 7.69 (8.00) |
| 30 | p-OCH₃ | 4-methylpiperazino | 138~140 | $C_{22}H_{25}N_3O_3$ | 69.63 (69.59) | 6.64 (6.68) | 11.08 (11.10) |
| 31 | H | thiomorpholino | 175~176 | $C_{19}H_{18}N_2O_2S$ | 67.43 (67.39) | 5.36 (5.35) | 8.28 (8.08) |
| 32 | H | N(CH₃)(CH₂)₂N(CH₃)₂·(CH₃)₂CO | 48~62 | $C_{21}H_{25}N_3O_2 \cdot (CH_3)_2CO$ | 70.39 (70.55) | 7.63 (7.54) | 10.26 (10.10) |
| 33 | H | 4-(3-trifluoromethylphenyl)piperazino·HCl | 102~135 | $C_{27}H_{24}F_3N_3O_2 \cdot HCl$ | 62.85 (62.88) | 4.88 (4.94) | 8.14 (8.12) |

*double melting point

EXAMPLE 5

3-(4-Benzylpiperazin-1-yl)carbonylmethyl-2-phenylisoindolin-1-one oxalate

An oily product (4.3 g), which was prepared from 2.67 g of 3-oxo-2-phenylisoindoline-1-acetic acid and 1.94 g of 1-benzylpiperazine in the same manner as Example 3, was dissolved in 4 ml of methanol, and to this solution a solution of 1.5 g of oxalic acid dihydrate in 6 ml of methanol was added, and the crystals precipitated were collected by filtration.

Yield, 4.90 g
m.p., 207°–210° C. (recrystallization from methanol).
Elemental analysis: Calcd. for $C_{27}H_{27}N_3O_2 \cdot C_2H_2O_4 \cdot \frac{1}{2}H_2O$: C, 66.40: H, 5.76: N, 8.01, Found: C, 66.26: H, 5.63: N, 8.17.

EXAMPLE 6

3-Oxo-2-phenylisoindoline-1-propionic acid (a) Ethyl 3-oxo-2-phenylisoindoline-1-acetate (5.9 g) was dissolved in tetrahydrofuran, 0.88 g of lithium borohydride was added to the solution, and the mixture was stirred for 48 hours, followed by decomposition treatment with 20% acetic acid and extraction with ethyl acetate. The extract was washed with water and dried. The solvent was then distilled off and the residue was treated with ethyl acetate-ether to give 4.1 g of crystals of 3-(2-hydroxyethyl)-2-phenylisoindolin-1-one, melted at 143°–144° C.

Elemental analysis: Calcd. for $C_{16}H_{15}NO_2$: C, 75.87: H, 5.97: N, 5.53, Found: C, 75.88: H, 5.87: N, 5.29.

(b) Mesyl chloride (4.1 ml) was added to a solution of 11.0 g of the above-obtained crystals and 9 ml of triethylamine in dichloromethane and the mixture was stirred for 10 minutes. The reaction mixture was washed with water, dried and concentrated, and the residue was treated with ether to give crystals (13.6 g) of 3-(2-mesyloxyethyl)-2-phenylisoindolin-1-one, melted at 100°–101° C.

Elemental analysis: Calcd. for $C_{17}H_{17}NO_4S$: C, 61.61: H, 5.17: N, 4.23. Found: C, 61.52: H, 4.98; N, 4.20.

(c) The above-obtained mesylate (4.97 g) was dissolved in aqueous alcohol, to the solution 3.0 g of potassium cyanide was added, and the mixture was refluxed for 3 hours. Water was added and the mixture was extracted with ethyl acetate, washed with water, dried and concentrated to give crystals (3.4 g) of 3-oxo-2-phenylisoindoline-3-propionitrile, melting at 144°–145° C.

Elemental analysis: Calcd. for $C_{17}H_{14}N_2O$: C, 77.84: H, 5.38: N, 10.68, Found: C, 77.71: H, 5.18: N, 10.55.

(d) The above-obtained nitrile (3.1 g) was dissolved in concentrated hydrochloric acid and the solution was refluxed for 15 hours. After cooling, the crystals precipitated were collected by filtration to give 3.3 g of 3-oxo-2-phenylisoindoline-1-propionic acid, melted at 186°–187° C.

Elemental analysis: Calcd. for $C_{17}H_{15}NO_3$: C, 72.58: H, 5.37: N, 4.98, Found: C, 72.49: H, 5.10: N, 4.99.

EXAMPLE 7

3-Piperidinocarbonylethyl-2-phenylisoindolin-1-one

Thionyl chloride (5 ml) was added to 1.4 g of 3-oxo-2-phenylisoindoline-1-propionic acid and the mixture was heated at 70° C. for 10 minutes. Removal of the excess thionyl chloride gave the corresponding acid chloride. The thus-obtained acid chloride was added to a mixture of 0.51 g of piperidine and 1.0 ml of triethylamine in dichloromethane and the mixture was stirred, washed with water, dried and the solvent was evaporated. The residue was treated with ethyl acetate to give crystals, melting at 144°–145° C.

EXAMPLE 8

3-(4-Methylpiperazin-1-yl)carbonylethyl-2-phenylisoindolin-1-one

Following the procedure of Example 7 but using N-methylpiperazine in lieu of piperidine, there was obtained the above-identified compound.
M.p. 204°–205° C.

EXAMPLE 9

3-Piperidinocarbonylmethyl-2-(5-chloro-2-pyridyl)isoindolin-1-one

3-Oxo-2-(5-chloro-2-pyridyl)isoindoline-1-acetic acid (1 g) and triethylamine (0.8 g) were dissolved in 20 ml of dry tetrahydrofuran and, under ice-cooling with stirring, 0.39 g of ethoxycarbonyl chloride was added portionwise. The mixture was stirred for 30 minutes, 0.56 g of piperidine was added, and the whole mixture was stirred for an additional 30 minutes. The reaction mixture was poured into 500 ml of ice water, followed by extraction with ethyl acetate. The extract was washed with water and dried. The ethyl acetate was then distilled off and the residue was treated with ether. The resulting crystals thus obtained were collected by filtration and recrystallized from ethyl acetate to give 0.32 g of colorless crystals, melted at 165°–166° C.

EXAMPLE 10

Following the procedure of Example 9 except that 4-methylpiperazine was used in lieu of piperidine, there was obtained 3-(4-methylpiperazin-1-yl)carbonylmethyl-2-(5-chloro-2-pyridyl)isoindolin-1-one.
M.p. 190°–193° C.

EXAMPLE 11

Methyl 3-oxo-2-(5-chloro-2-pyridyl)isoindoline-1-acetate

To 1 g of 3-oxo-2-(5-chloro-2-pyridyl)isoindoline-1-acetic acid was added 20 ml of 10% methanolic hydrochloric acid and the mixture was refluxed. After 5 hours, the reaction mixture was concentrated under reduced pressure, 100 ml of aqueous sodium hydrogen carbonate solution was added to the residue and the mixture was extracted with ethyl acetate. The extract was washed with water, dried and concentrated to give about 1 g of crystals, which were recrystallized from ethyl acetate-ether.
M.p. 110°–111° C.
Elemental analysis: Calcd. for $C_{16}H_{13}N_2O_3Cl$: C, 60.67: H, 4.13: N, 8.84, Found: C, 60.50: H, 4.13: N, 8.78.

EXAMPLE 12

In the same manner as Example 11, there was obtained the following compound:
(i) Methyl 3-oxo-2-(4-methoxyphenyl)isoindoline-1-acetate
M.p. 80° C.
Elemental analysis: Calcd. for $C_{18}H_{17}NO_4$: C, 69.44: H, 5.50: N, 4.50, Found: C, 69.56: H, 5.07: N, 5.62.

EXAMPLE 13

In the same manner as (a)-(c) of Example 1, there were obtained the following compounds:
(i) Ethyl 3-oxo-2-(3-chlorophenyl)isoindoline-1-acetate
M.p. 82°-83° C.
Elemental analysis: Calcd. for $C_{18}H_{16}NO_3Cl$: C, 65.55: H, 4.89: N, 4.24, Found: C, 65.51: H, 4.73: N, 4.11.
(ii) Ethyl 3-oxo-2(4-chlorophenyl)isoindoline-1-acetate
M.p. 55°-56° C.
Elemental analysis: Calcd. for $C_{18}H_{16}NO_3Cl$: C, 65.55: H, 4.89: N, 4.24, Found: C, 65.27: H, 4.64: N, 4.00.

EXAMPLE 14

3-Hydroxy-2-(3,4,5-trimethoxyphenyl)isoindolin-1-one (1.1 g) and piperidinocarbonylmethylenetriphenylphosphorane (1.8 g) were dissolved in 20 ml of toluene and the solution was refluxed for 2 hours. After cooling, the toluene was distilled off and ether was added to the residue to give crude crystals, which were crystallized from ether giving 1.0 g of 2-(3,4,5-trimethoxyphenyl)-3-piperidinocarbonylmethylisoindolin-1-one.
M.p. 84°-86° C.
Elemental analysis: Calcd. for $C_{24}H_{28}N_2O_5$: C, 67.90: H, 6.65: N, 6.60, Found: C, 67.88: H, 6.66: N, 6.56.

EXAMPLE 15

In the same manner as Example 12, there were obtained the compounds listed in Table 3.

TABLE 3

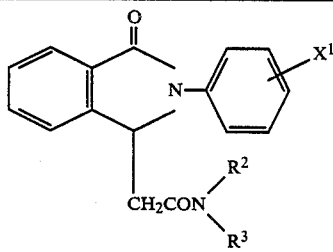

| No | $X^1$ | $\mathrm{N}\begin{smallmatrix}R^2\\R^3\end{smallmatrix}$ | M.p. [°C.] | molecular formula | Elemental analysis Calcd. (Found) C | H | N |
|---|---|---|---|---|---|---|---|
| 1 | P—OCH$_3$ | (azepane) | 119~120 | $C_{23}H_{26}N_2O_3$ | 72.99 (73.23) | 6.93 (6.98) | 7.40 (7.28) |
| 2 | P—OCH$_3$ | (thiomorpholine) | 139~140 | $C_{20}H_{20}N_2O_3S$ | 65.20 (65.16) | 5.47 (5.45) | 7.60 (7.46) |
| 3 | P—NO$_2$ | (piperidine) | 168~176 | $C_{21}H_{21}N_3O_4$ | 66.48 (66.10) | 5.58 (5.54) | 11.07 (10.90) |
| 4 | P—OH | (piperidine) | 216~220 | $C_{21}H_{22}N_2O_3$ | 71.98 (71.80) | 6.33 (6.25) | 7.99 (7.58) |
| 5 | P—CO$_2$C$_2$H$_5$ | (piperidine) | 144~145 | $C_{23}H_{24}N_2O_4$ | 70.39 (70.30) | 6.16 (6.07) | 7.14 (7.05) |
| 6 | P—NH$_2$.HCl | (piperidine) | 176~186 | $C_{21}H_{23}N_3O_2$.HCl | 65.36 (65.39) | 6.27 (6.24) | 10.89 (10.81) |
| 7 | P—NHCOCH$_3$ | (piperidine) | 183~185 | $C_{23}H_{25}N_3O_3$ | 70.57 (70.41) | 6.44 (6.44) | 10.73 (10.68) |

TABLE 3-continued

[Structure: 2-[2-(1-methyl-2-(N,N-disubstituted-carbamoylmethyl)ethyl)phenyl]-N-(substituted phenyl)acetamide type structure with X¹ on aniline and CH₂CON(R²)(R³) group]

| No | X¹ | NR²R³ | M.p. [°C.] | molecular formula | Elemental analysis Calcd. (Found) | | |
|---|---|---|---|---|---|---|---|
| 8 | P—OC₂H₅ | piperidino | 118~120 | $C_{23}H_{26}N_2O_3$ | 72.99 (72.77) | 6.92 (6.86) | 7.40 (7.25) |
| 9 | P—OCH₂Ph | piperidino | 171~173 | $C_{28}H_{28}N_2O_3$ | 76.34 (76.61) | 6.41 (6.46) | 6.36 (6.18) |
| 10 | P—NO₂ | 4-methylpiperazino | 208~210 | $C_{21}H_{22}N_4O_4$ | 63.95 (63.73) | 5.62 (5.71) | 14.20 (14.14) |
| 11 | P—CH₃ | piperidino | 142~144 | $C_{22}H_{24}N_2O_2$ | 75.83 (75.87) | 6.94 (7.03) | 8.04 (8.22) |
| 12 | P—CO₂H | piperidino | 198~199 | $C_{22}H_{22}N_2O_4$ | 69.82 (69.64) | 5.86 (5.94) | 7.40 (7.25) |
| 13 | P—O—n-C₄H₉ | piperidino | 59~62, 64~66 * | $C_{25}H_{30}N_2O_3$ | 73.86 (74.14) | 7.44 (7.61) | 6.89 (6.95) |
| 14 | P—CH(OH)CH₃ | piperidino | 168~174 | $C_{23}H_{26}N_2O_3$ | 72.99 (72.76) | 6.92 (6.91) | 7.40 (7.23) |
| 15 | P—CH₃ | 4-methylpiperazino·½H₂O | 160~161 | $C_{22}H_{25}N_3O_2·½H_2O$ | 70.94 (71.19) | 7.04 (6.60) | 11.28 (11.28) |
| 16 | P—OH | hexamethyleneimino | 205~207 | $C_{22}H_{24}N_2O_3$ | 72.51 (72.76) | 6.64 (6.44) | 7.69 (7.95) |
| 17 | P—F | piperidino | 113~114.5 | $C_{21}H_{21}FN_2O_2$ | 71.57 (71.81) | 6.01 (5.84) | 7.95 (8.13) |

TABLE 3-continued

[Structure: isoindolin-1-one core with N-phenyl substituent bearing X¹, and CH₂CON(R²)(R³) group]

| No | X¹ | N(R²)(R³) | M.p. [°C.] | molecular formula | Elemental analysis Calcd. (Found) | | |
|---|---|---|---|---|---|---|---|
| 18 | P—(CH₂)₂OCOH₃ | piperidino | 104~105 | $C_{25}H_{28}N_2O_4$ | 71.41 (71.60) | 6.71 (6.60) | 6.66 (6.81) |
| 19 | P—(CH₂)₂—OH | piperidino | 153~155 | $C_{23}H_{26}N_2O_3$ | 72.99 (72.72) | 6.98 (6.86) | 7.40 (7.43) |
| 20 | m-CF₃ | piperidino | 108~110 | $C_{22}H_{21}F_3N_2O_2$ | 65.66 (65.54) | 5.26 (5.55) | 6.96 (6.87) |
| 21 | 3.4-diOCH₃ | piperidino | 119~120 | $C_{23}H_{26}N_2O_4$ | 70.03 (69.73) | 6.64 (6.78) | 7.10 (7.09) |
| 22 | 3.5-diOCH₃ | piperidino | 122~123 | $C_{23}H_{26}N_2O_4$ | 70.03 (69.98) | 6.64 (6.49) | 7.10 (7.15) |
| 23 | 2.5-diOCH₃ | piperidino | oil | $C_{23}H_{26}N_2O_4$ | 70.03 (69.89) | 6.64 (6.61) | 7.10 (7.12) |
| 24 | 4-CONH₂ | piperidino | 210~211 | $C_{22}H_{23}N_3O_3$ | 70.01 (69.69) | 6.14 (6.05) | 11.13 (11.23) |
| 25 | P—CH₂CH₂Cl | piperidino | 100~105 | $C_{23}H_{25}ClN_2O_2$ | 69.60 (69.37) | 6.35 (6.43) | 7.06 (6.96) |

* double melting point

EXAMPLE 16

(i) A solution of 3-hydroxy-2-(4-methoxyphenyl)isoindolin-1-one (12.0 g) and ethoxycarbonylmethylenetriphenylphosphorane (16.0 g) in toluene (200 ml) was refluxed for 3 hours. After cooling, the toluene was distilled off and the residue was dissolved in 100 ml of methanol. A solution of 10 g of potassium carbonate in 70 ml of water was added to the above methanol solution and the mixture was refluxed gently for an hour. After cooling, 200 ml of water and 300 ml of ether were added and the mixture was shaken well. The aqueous layer was separated and acidified with 5N hydrochloric acid to give 12 g of 3-oxo-2-(4-methoxyphenyl)isoindoline-1-acetic acid, which was described in (iv) of Example 2.

(ii) The above acetic acid derivative (6.53 g) was dissolved in 30 ml of thionyl chloride and the solution was refluxed gently for 10 minutes. After cooling, the excess thionyl chloride was distilled off under reduced pressure to give the corresponding acid chloride. Without purification, the product was dissolved in 100 ml of dichloromethane and a solution of 3.12 g of l-menthol in pyridine (100 ml) was added portionwise under cooling with ice water. After 3 hours, 400 ml of ice water was added, followed by extraction with dichloromethane. The dichloromethane layer was washed with water, dried over anhydrous sodium sulfate. The solvent was evaporated off to give 7.9 g of crude crystals. This product is a diastereoisomer of the l-menthyl ester.

(iii) The above l-menthyl ester (7.9 g) was separated into two pure diastereoisomers by fractional recrystallization from ethyl acetate.

(A)  (−)-3-Oxo-2-(4-methoxyphenyl)isoindoline-1-acetic acid l-menthyl ester

M.p.: 179.5°–180.5° C.

Elemental analysis: Calcd. for $C_{27}H_{33}NO_4$: C, 74.45; H, 7.64; N, 3.22 Found: C, 74.60; H, 7.66; N, 3.18.

Optical rotation: $[\alpha]_D^{23} -82.6°$ (C=1.0 in chloroform).

(B) [+]-3-Oxo-2-(4-methoxyphenyl)isoindoline-1-acetic acid l-menthyl ester.

M.p.: 199°–200° C.

Elemental analysis: Calcd. for $C_{27}H_{33}NO_4$: C, 74.45; H, 7.64; N, 3.22, Found: C, 74.65; H, 7.64; N, 3.17.

Optical rotation: $[\alpha]_D^{23} +40.7°$ (C=1.0 in chloroform)

(iv) The above ester compounds (A) and (B) were respectively hydrolyzed with 35% HCl in dioxane to give optically active carboxylic acids without racemization (recrystallization from methanol).

(A)  (−)-3-Oxo-2-(4-methoxyphenyl)isoindoline-1-acetic acid

M.p.: 245°–246° C.

Elemental analysis: Calcd. for $C_{17}H_{15}NO_4$: C, 68.67; H, 5.08; N, 4.71, Found: C, 68.59; H, 5.04; N, 4.70.

Optical rotation: $[\alpha]_D^{23} -60.3°$ (C=0.5 in methanol)

(B)  (+)-3-Oxo-2-(4-methoxyphenyl)isoindoline-1-acetic acid

M.p.: 245°–246° C.

Elemental analysis: Calcd. for $C_{17}H_{15}NO_4$: C, 68.67; H, 5.08; N, 4.71, Found: C, 68.55; H, 5.02; N, 4.72.

Optical rotation: $[\alpha]_D^{23} +60.2°$ (C=0.5 in methanol)

(v) To a solution of (−) acetic acid ester (A) obtained above in dimethylformamide was added 1 equivalent of piperidine and 1.2 equivalents of diethyl phosphorocyanidate at 0° C., further followed by addition of triethylamine. After the mixture was stirred for 15 minutes, water was added, and the product was carried out with dichloromethane. The dichloromethane layer was extracted with water, dried over anhydrous sodium sulfate and the solvent was evaporated to give crude crystals. Recrystallization from ether gave the desired compound in optically active form in good yield.

(A′)  (−)-2-(4-Methoxyphenyl)-3-piperidinocarbonylmethylisoindolin-1-one

M.p.: 110°–111° C.

Elemental analysis: Calcd. for $C_{22}H_{24}N_2O_3$: C, 72.50; H, 6.64; N, 7.69, Found: C, 72.69; H, 6.65; N, 7.60.

Optical rotation: $[\alpha]_D^{23} -134°$ (C=1.0 in chloroform)

(vi) The above (+) acetic acid ester (B) was worked up in the same manner as (v) to give the following compound:

(B′)  (+)-2-(4-Methoxyphenyl)-3-piperidinocarbonylmethylisoindolin-1-one

M.p.: 110°–111° C.

Elemental analysis: Calcd. for $C_{22}H_{24}N_2O_3$: C, 72.50; H, 6.64; N, 7.69, Found: C, 72.55; H, 6.64; N, 7.66.

Optical rotation: $[\alpha]_D^{23} +135°$ (C=1.0 in chloroform)

EXAMPLE 17

A solution of 1.2 g of 2-cyclohexyl-3-hydroxyisoindolin-1-one and 2.2 g of piperidinocarbonylmethylenetriphenylphosphorane in toluene (30 ml) was refluxed for 3 hours. After cooling, the toluene was distilled off and ether was added whereupon triphenylphosphine oxide separated out. After filtration, the filtrate was allowed to stand to giving crude crystals. Recrystallization from ether gave 1.3 g of 2-cyclohexyl-3-piperidinocarbonylmethylisoindolin-1-one.

M.p.: 158.5°–159.5° C.

Elemental analysis: Calcd. for $C_{21}H_{28}N_2O_2$: C, 74.08; H, 8.29; N, 8.23, Found: C, 74.16; H, 8.00; N, 8.20.

EXAMPLE 18

(a) 2,3,6,7-Tetrahydro-6-(4-methoxyphenyl)-5H-1,4-dithiino[2,3-C]pyrrole-5,7-dione (8.50 g) was suspended in methanol-tetrahydrofuran (1:1, 80 ml) and, under ice-cooling and stirring, sodium borohydride (0.88 g) was added. The mixture was stirred for about 3 hours and then poured into ice water. After extraction with ethyl acetate, the extract was washed with water, dried (over $Na_2SO_4$) and evaporated to give 2,3,6,7-tetrahydro-7-hydroxy-6-(4-methoxyphenyl)-5H-1,4-dithiino[2,3-C]pyrrol-5-one (8.40 g) as crystals.

M.p.: 153°–154° C.

Elemental analysis: Calcd. for $C_{13}H_{13}NO_3S_2$: C, 52.86; H, 4.44; N, 4.74, Found: C, 52.63; H, 4.40; N, 4.60.

2,3,6,7-Tetrahydro-6-(4-methoxyphenyl)-5H-1,4-dithiino[2,3-C]pyrrole-5,7-dione which was used as the starting compound was prepared by the method of H. R. Schweizer [Helv. Chim. Acta, 52, 2221 (1969)].

M.p.: 181°–182° C.

(b) 2,3,6,7-Tetrahydro-7-hydroxy-6-(4-methoxyphenyl)-5H-1,4-dithiino[2,3-C]pyrrol-5-one (1.48 g) and piperidinocarbonylmethylenetriphenylphosphorane (3.4 g) were dissolved in toluene (30 ml) under heating, and the solution was refluxed for 12 hours. The reaction mixture was concentrated and the residue was subjected to silica gel column chromatography (methylene chloride:ethyl acetate=10:1). The thus-obtained crude crystals were recrystallized from ethyl acetate-ether to give crystals (1.45 g) of 2,3,6,7-tetrahydro-6-(4-methoxyphenyl)-7-piperidinocarbonylmethyl-5H-1,4-dithiino[2,3-C]pyrrol-5-one, melting at 163°–164° C. and 183°–185° C. (double melting).

Elemental analysis: Calcd. for $C_{20}H_{24}N_2O_3S_2$: C, 59.38; H, 5.98; N, 6.93, Found: C, 59.32; H, 5.97; N, 6.71.

EXAMPLE 19

In the same manner as Example 18, there were obtained the compounds given in Table 4.

TABLE 4

[Structure: bicyclic dithiin fused with N-aryl lactam bearing CH₂CON(R²)(R³) substituent and X¹ on phenyl]

| No. | X¹ | NR²R³ | M.p. [°C.] | molecular formula | Elemental analysis Calcd. (Found) C | H | N |
|---|---|---|---|---|---|---|---|
| 1 | p-Cl | piperidinyl | 186~189 | C₁₉H₂₁ClN₂O₂S₂ | 55.80 (55.87) | 5.18 (5.06) | 6.85 (6.82) |
| 2 | p-Cl | hexamethyleneimino | 182~183 | C₂₀H₂₃ClN₂O₂S₂ | 56.79 (56.73) | 5.48 (5.46) | 6.62 (6.54) |
| 3 | p-OCH₃ | hexamethyleneimino | 135~136 / 147~148 * | C₂₁H₂₆N₂O₃S₂ | 60.26 (60.54) | 6.26 (6.22) | 6.69 (6.67) |
| 4 | H | piperidinyl | 200 | C₁₉H₂₂N₂O₂S₂ | 60.93 (61.01) | 5.92 (6.03) | 7.48 (7.45) |
| 5 | H | hexamethyleneimino | 152~153 | C₂₀H₂₄N₂O₂S₂ | 61.82 (61.93) | 6.23 (6.40) | 7.21 (7.22) |
| 6 | p-OCH₃ | piperidinyl | 173~175 | C₁₉H₂₂N₂O₃S₂ | 58.43 (58.20) | 5.68 (5.69) | 7.17 (7.08) |
| 7 | p-Cl | pyrrolidinyl | 185~186 | C₁₈H₁₉ClN₂O₂S₂ | 54.74 (54.89) | 4.85 (4.80) | 7.09 (7.14) |
| 8 | H | pyrrolidinyl | 204 | C₁₈H₂₀N₂O₂S₂ | 59.97 (59.90) | 5.59 (5.56) | 7.77 (7.68) |
| 9 | p-OCH₃ | 4-methylpiperazinyl | 109~114 | C₂₀H₂₅N₃O₃S₂ | 57.26 (57.09) | 6.01 (5.84) | 10.02 (10.16) |
| 10 | p-OCH₃ | N(C₂H₅)₂ | 167~168 | C₁₉H₂₄N₂O₃S₂ | 58.13 (58.08) | 6.16 (5.97) | 7.14 (7.19) |
| 11 | p-OCH₃ | NH-C₆H₄-F (4-F) | 204~206 | C₂₁H₁₉FN₂O₃S₂ | 58.59 (58.50) | 4.45 (4.50) | 6.51 (6.50) |

TABLE 4-continued

[Structure: a bicyclic compound with S-S ring fused to a pyridinone ring bearing N-aryl(X¹) and CH2CON(R²)(R³) substituents]

| No. | X¹ | N(R²)(R³) | M.p. [°C.] | molecular formula | Elemental analysis Calcd. (Found) | | |
|---|---|---|---|---|---|---|---|
| 12 | p-OCH₃ | thiomorpholino (N–CH₂CH₂–S–CH₂CH₂) | 157~158 | $C_{18}H_{20}N_2O_3S_3$ | 52.92 (52.58) | 4.93 (4.71) | 6.86 (6.77) |
| 13 | p-OCH₃ | morpholino | 142~144 | $C_{19}H_{22}N_2O_4S_2$ | 56.14 (55.87) | 5.46 (5.25) | 6.89 (6.64) |
| 14 | p-Cl | 4-phenylpiperazino (N–N–Ph) | 183~184 | $C_{24}H_{24}ClN_3O_2S_2$ | 59.30 (59.04) | 4.98 (4.93) | 8.65 (8.61) |
| 15 | p-OCH₃ | 4-(4-fluorophenyl)piperazino | 193~194 | $C_{25}H_{26}FN_3O_3S_2$ | 60.10 (60.13) | 5.25 (5.18) | 8.41 (8.43) |
| 16 | p-OCH₃ | N(CH₃)(CH₂–Ph) | 152~153 | $C_{23}H_{24}N_2O_3S_2$ | 62.70 (62.74) | 5.49 (5.39) | 6.36 (6.52) |

*double melting point

EXAMPLE 20

6-(5-Chloro-2-pyridyl)-6,7-dihydro-7-hydroxy-5H-pyrrolo[3,4-b]pyrazin-5-one (786 mg) and piperidinocarbonylmethylenetriphenylphosphorane (1.17 g) were dissolved in dry toluene (15 ml) and the solution was refluxed for 6 hours. After cooling, the solvent was distilled off and ether was added to the residue to give crude crystals. The cyrstals were collected by filtration and recrystallized from dichloromethane-ether (1:5) to give 921 mg of 6-(5-chloro-3-pyridyl)-6,7-dihydro-7-piperidinocarbonylmethyl-5H-pyrrolo[3,4-b]pyrazin-5-one.

M.p.: 212°–213° C.

Elemental analysis: Calcd. for $C_{18}H_{18}ClN_5O_2$: C, 58.14; H, 4.88; N, 18.84, Found: C, 58.15; H, 4.97; N, 18.81.

EXAMPLE 21

(a) 6-(5-Chloro-2-pyridyl)-6,7-dihydro-7-hydroxy-5H-pyrrolo[3,4-b]pyrazin-5-one (1.05 g) and ethoxycarbonylmethylenetriphenylphosphorane (1.39 g) were dissolved in dry toluene (30 ml) and the solution was refluxed for 6 hours. After cooling, the solvent was distilled off and the residue was purified by silica gel column chromatography. Fractions eluted with dichloromethane-ethyl acetate (2:1) were collected and the solvent was distilled off to give crude crystals. Recrystallization from ether-dichloromethane (5:1) gave 1.2 g of 6-(5-chloropyridyl)-6,7-dihydro-7-ethoxycarbonylmethyl-5H-pyrrolo[3,4-b]pyrazin-5-one.

M.p.: 170°–171° C.

Elemental analysis: Calcd. for $C_{15}H_{13}ClN_4O_3$: C, 54.14; H, 3.94; N, 16.84, Found: C, 54.01; H, 4.00; N, 16.84.

(b) The compound (1.2 g) as obtained above in (a) was dissolved in 30 ml of methanol, to the solution 200 mg of sodium hydroxide was added and the mixture was heated at 60° C. After 1 hour, the reaction mixture was neutralized with 3N hydrochloric acid-methanol and the resulting sodium chloride precipitated was filtered off. The filtrate was then concentrated to give a crystalline residue which was crude 6-(5-chloro-2-pyridyl)-6,7-dihydro-5H-pyrrolo[3,4-b]pyrazin-5-one-7-acetic acid. This product was not purified, but dissolved in 20 ml of dry dimethylformamide. The solution was ice-cooled, and thereto were added 0.5 g of N-methylpiperazine and 0.5 ml of triethylamine, and then 0.82 g of diethyl phosphorocyanidate. The mixture was stirred under ice-cooling for 3 hours. To the reaction mixture was added 100 ml of water, followed by extraction with dichloromethane. The dichloromethane layer was washed with water and dried over anhydrous sodium sulfate. The solvent was then distilled off to give crude crystals. This product was recrystallized from ether-dichloromethane (3:1) to give 1.0 g of 6-(5-chloro-2-pyridyl)-6,7-dihydro-7-(4-methylpiperazin-1-yl)carbonylmethyl-5H-pyrrolo[3,4-b]pyrazin-5-one hemihydrate.

M.p.: 244°–246° C.

Elemental analysis: Calcd. for $C_{18}H_{19}ClN_6O_2 \cdot \frac{1}{2}H_2O$: C, 54.61; H, 5.09; N, 21.23, Found: C, 54.80; H, 4.74; N, 21.21.

EXAMPLE 22

2-(4-Methoxyphenyl)-3-hydroxy-4,5,6,7-tetrahydroisoindolin-1-one (2.59 g) and piperidinocarbonylmethylenetriphenylphosphorane (4.6 g) were dissolved in 50 ml of dry toluene and the solution was refluxed gently for 20 hours. After cooling, the solvent was distilled off and the residue was purified by silica gel column chromatography. Fractions eluted with dichloromethaneethyl acetate (5:1) were collected and concentrated to give crude crystals. This product was recrystallized from ether-hexane (1:3) to give 1.87 g of 2-(4-methoxyphenyl)-3-piperidinocarbonylmethyl-4,5,6,7-tetrahydroisoindolin-1-one.

M.p.: 101°–102° C.

Elemental analysis: Calcd. for $C_{22}H_{28}N_2O_3$: C, 71.71; H, 7.66; N, 7.60, Found: C, 71.83; H, 7.59; N, 7.75.

EXAMPLE 23

2-(4-Chlorophenyl)-3-hydroxy-4,5,6,7-tetrahydroisoindolin-1-one was worked up in the same manner as Example 22 to give 2-(4-chlorophenyl)-3-piperidinocarbonylmethyl-4,5,6,7-tetrahydroisoindolin-1-one.

M.p.: 120°–122° C.

Elemental analysis: Calcd. for $C_{21}H_{25}ClN_2O_2$: C, 67.64; H, 6.75; N, 7.51, Found: C, 67.91; H, 6.74; N, 7.58.

EXAMPLE 24

2-(4-Chlorophenyl)-3-hydroxy-4,5,6,7-tetrahydroisoindolin-1-one was worked up in the same manner as Example 22 to give 2-(4-chlorophenyl)-3-hexamethyleneiminocarbonylmethyl-4,5,6,7-tetrahydroisoindolin-1-one.

M.p.: 169°–170° C.

Elemental analysis: Calcd. for $C_{22}H_{27}ClN_2O_2$: C, 68.29; H, 7.03; N, 7.24, Found: C, 68.46; H, 6.87; N, 7.28.

EXAMPLE 25

In the same manner as Example 22, there were obtained the following compounds:
(i) 2-(4-Methoxyphenyl)-3-pyrrolidinocarbonylmethyl-4,5,6,7-tetrahydroisoindolin-1-one M.p.: 114°–115° C.

Elemental analysis: Cald. for $C_{21}H_{26}N_2O_3$: C, 71.16; H, 7.39; N, 7.90, Found: C, 71.19; H, 7.21; N, 8.05.
(ii) 2-(2-Methoxyphenyl)-3-hexamethyleneiminocarbonylmethyl-4,5,6,7-tetrahydroisoindolin-1-one M.p.: 113°–114° C.

Elemental analysis: Cald. for $C_{23}H_{30}N_2O_3$: C, 72.22; H, 7.91; N, 7.32, Found: C, 72.30; H, 7.80; N, 7.31.

EXAMPLE 26

(i) Ethoxycarbonylmethylenetriphenylphosphorane (3.0 g) was added to a solution of 2-(4-methoxyphenyl)-3-hydroxy-4,5,6,7-tetrahydroisoindolin-1-one (2.59 g) in toluene (30 ml) and the solution was refluxed gently for 48 hours. After cooling, the solvent was distilled off and the residue was dissolved in 30 ml of methanol. Potassium carbonate (3 g) and water (10 ml) were added and the mixture was refluxed for an hour. After cooling, the methanol was distilled off, 100 ml of water and 100 ml of dichloromethane were added and the mixture was stirred well. The aqueous layer was separated and acidified with 5% hydrochloric acid to give crystals, which was washed with water, dried and recrystallized from methanol-ether (1:3) to give 24.6 g of 2-(4-methoxyphenyl)-3-oxo-4,5,6,7-tetrahydroisoindoline-1-acetic acid.

M.p.: 203°–204° C.

Elemental analysis: Calcd. for $C_{17}H_{19}NO_4$: C, 67.76; H, 6.36; N, 4.65, Found: C, 68.01; H, 6.40; N, 4.91.

(ii) In the same manner as above, there was obtained 2-(4-chlorophenyl)-3-oxo-4,5,6,7-tetrahydroisoindoline-1-acetic acid.

M.p.: 177°–178° C.

Elemental analysis: Calcd. for $C_{16}H_{16}ClNO_3$: C, 62.85; H, 5.27; N, 4.58, Found: C, 62.88; H, 5.15; N, 4.68.

EXAMPLE 27

2-(4-Methoxyphenyl)-5-nitro-3-piperidinocarbonylmethylisoindolin-1-one and
2-(4-methoxyphenyl)-6-nitro-3-piperidinocarbonylmethylisoindolin-1-one N-(4-methoxyphenyl)-4-nitrophthalamide (12 g) was suspended in a mixture of methanol (80 ml) and tetrahydrofuran (80 ml) and, under ice-cooling and stirring, sodium borohydride (1.6 g) was added. Water (300 ml) was added to the mixture and crude crystals were collected by filtration to give a mixture (11 g) of 3-hydroxy-2-(4-methoxyphenyl)-5-nitroisoindolin-1-one and 3-hydroxy-2-(4-methoxyphenyl)-6-nitroisoindolin-1-one. The mixture (6.0 g) thus obtained and piperidinocarbonylmethylenetriphenylphosphoran (9.3 g) were dissoleved in toluene (200 ml) under heating, and the solution was refluxed for 3 hours. After cooling, crystals separated were collected by filtration and recrystallized from toluene to give 2.2 g of 2-(4-methoxyphenyl)-6-nitro-3-piperidinocarbonylmethylisoindolin-1-one.

M.p.: 209°–210° C.

Elemental analysis: Calcd. for $C_{22}H_{23}N_3O_5$: C, 64.53; H, 5.66; N, 10.26, Found: C, 64.37; H, 5.51; N, 10.24.

NMR δ(in $CDCl_3$): 7.88 (1H, d, 4-H), 8.38 (1H, dd, 5-H), 8.65 (1H, d, 7-H).

The mother liquor obtained above was concentrated and the residue was subject to purify by column chromatography on silica gel and eluted with toluene-ethyl acetate.

Crude crystals obtained from initially eluted fractions were recrystallized from ethyl acetate to give 2.0 of the corresponding 5-nitro compound.

M.p.: 187°–189° C.

Elemental analysis: Calcd.: for $C_{12}H_{23}N_3O_5$: C, 64.53; H, 5.66; N, 10.26. Found: C, 64.26; H, 5.57; N, 10.22.

NMR δ(in $CDCl_3$: 8.01 (1H, d, 7-H), 8.34 (1H, dd, 6-H), 8.52(1H, d, 4-H).

From the subsequent fractions a mixture (2.4 g) of 5-nitro compound and 6-nitro compound was obtained. Crude crystals obtained from further subsequent fractions were recrystallized from toluene to give 1.0 g of 6-nitro compound.

EXAMPLE 28

In the same manner as Example 27, there were obtained the compounds listed in Table 5.

TABLE 5

| No. | $X_1$ | $X_2$ | $N\underset{R^3}{\overset{R^2}{\diagdown}}$ | M.P. [°C.] | molecular formula | Elemental analysis Calcd. (Found) C | H | N |
|---|---|---|---|---|---|---|---|---|
| 1. | p-OCH$_3$ | 4-NO$_2$ | piperidino | 197~198 | C$_{22}$H$_{23}$N$_3$O$_5$ | 64.53 (64.52) | 5.66 (5.93) | 10.26 (10.33) |
| 2. | p-OCH$_3$ | 5-NH$_2$ | piperidino | 239~243 | C$_{22}$H$_{25}$N$_3$O$_3$·¼H$_2$O | 68.82 (68.96) | 6.69 (6.85) | 10.95 (10.81) |
| 3. | p-OCH$_3$ | 6-NH$_2$ | piperidino | 198~200 | C$_{22}$H$_{25}$N$_3$O$_3$·¼H$_2$O | 68.82 (69.09) | 6.69 (6.72) | 10.95 (10.76) |
| 4. | p-OCH$_3$ | 5-NHAc | piperidino | 198~222 | C$_{24}$H$_{27}$N$_3$O$_4$ | 68.39 (68.23) | 6.46 (6.41) | 9.97 (9.75) |
| 5. | p-OCH$_3$ | 5-NHAc | piperidino | 250~252 | C$_{24}$H$_{27}$N$_3$O$_4$ | 68.39 (68.27) | 6.46 (6.50) | 9.97 (9.78) |
| 6. | p-OCH$_3$ | 5-Cl | piperidino | 153~154 | C$_{22}$H$_{23}$ClN$_2$O$_3$ | 66.24 (66.27) | 5.81 (5.89) | 7.02 (7.00) |
| 7. | p-OCH$_3$ | 6-Cl | piperidino | 144~146 | C$_{22}$H$_{23}$ClN$_2$O$_3$ | 66.24 (66.31) | 5.81 (5.79) | 7.02 (7.10) |
| 8. | p-OCH$_3$ | 6-COOCH$_3$ | piperidino | 139~141 } * 162~164 } | C$_{24}$H$_{26}$N$_2$O$_5$ | 68.23 (68.27) | 6.20 (6.19) | 6.63 (6.56) |
| 9. | p-OCH$_3$ | 6-CONH$_2$ | piperidino | 273~280 | C$_{23}$H$_{25}$N$_3$O$_4$ | 67.79 (67.76) | 6.18 (6.11) | 10.31 (10.22) |
| 10. | p-OCH$_3$ | 6-COOH | piperidino | 232~236 | C$_{23}$H$_{24}$N$_2$O$_5$ | 67.63 (67.72) | 5.92 (5.76) | 6.86 (6.79) |

TABLE 5-continued

[Structure: X₂-substituted benzene fused to a ring containing C=O, N-aryl(X₁), and CH₂CON(R²)(R³) substituent]

| No. | X₁ | X₂ | N(R²)(R³) | M.P. [°C.] | molecular formula | Elemental analysis Calcd. (Found) | | |
|---|---|---|---|---|---|---|---|---|
| 11. | p-OCH₃ | 5-COOH | piperidino | 249~256 | $C_{23}H_{24}N_2O_5$ | 67.63 (67.51) | 5.92 (5.89) | 6.86 (6.62) |
| 12. | p-OCH₃ | 5,6-di-Cl | piperidino | 172~174 | $C_{22}H_{22}Cl_2N_2O_3$ | 60.97 (60.86) | 5.12 (5.14) | 6.47 (6.31) |
| 13. | p-OCH₃ | 5-Cl | 4-methylpiperazino | 169~171 | $C_{22}H_{24}ClN_3O_3$ | 63.84 (63.88) | 5.84 (5.80) | 10.15 (10.09) |

*double melting point

EXAMPLE 29

In the same manner as Example 14, 2-(7-chloro-1,8-naphthyridin-2-yl)-3-piperidinocarbonylmethylisoindolin-1-one was obtained from 2-(7-chloro-1,8-naphthyridin-2-yl)-3-hydroxyisoindolin-1-one.

M.p.: 217°-218° C.

Elemental analysis: Calcd. for $C_{23}H_{21}ClN_4O_2$: C, 65.63; H, 5.03; N, 13.31, Found: C, 65.88; H, 4.93; N, 13.40.

EXAMPLE 30

In the same manner as Example 18, 2,3,6,7-tetrahydro-6-(4-fluorophenyl)-7-piperidinocarbonylmethyl-5H-1,4-dithiino[2,3-c]pyrrol-5-one was obtained from 2,3,6,7-tetrahydro-b 7-hydroxy-6-(4-fluorophenyl-5H-1,4-dithiino[2,3-c]pyrrol-5-one.

M.p.: 173°-192° C.

Elemental analysis: Calcd. for $C_{19}H_{21}FN_2O_2S_2$: C, 58.14; H, 5.39; N, 7.14, Found: C, 58.13; H, 5.21; N, 7.10.

EXAMPLE 31

(i) In a similar manner to Example 16, 2,3,6,7-tetrahydro-6-(4-methoxyphenyl)-5-oxo-5H-1,4-dithiino[2,3-c]pyrrol-7-acetic acid was resolved by the conventional method using cinchonine and optically active (—)-2,3,6,7-tetrahydro-6-(4-methoxyphenyl)-5-oxo-5H-1,4-dithiino[2,3-c]pyrrol)-7-acetic acid was obtained.

Optical rotation: $[\alpha]_D^{23} = -58.6°$ (C=1.0 in methanol).

M.p.: 204°-205° C.

Elemental analysis Calcd. for $C_{15}H_{15}NO_4S_2$: C, 53.39; H, 4.48; N, 4.15, Found: C, 53.62; H, 4.43; N, 4.03.

(ii) The (—)-carboxylic acid obtained above was worked up in the same manner as Example 16 (v) to give (—)-2,3,6,7-tetrahydro-6-(4-methoxyphenyl)-7-piperidinocarbonylmethyl-5H-1,4-dithino[2,3-c]pyrrol-5-one.

Optical rotation: $[\alpha]_D^{23} = -156°$ (C=0.1 in chloroform).

M.p.: 191°-192° C.

Elemental analysis Calcd. for $C_{20}H_{24}N_2O_3S_2$: C, 59.38; H, 5.98; N, 6.93, Found: C, 59.36; H, 5.99; N, 6.84.

EXAMPLE 32

In the same manner as Example 21, 2-(7-chloro-1,8-naphthyridin-2-yl)-3-(4-methylpiperadin-1-yl)carbonylmethylisoindolin-1-one was obtained from 3-oxo-2-(7-chloro-1,8-naphthyridin-2-yl)isoindoline-1-acetic acid and N-methylpiperadine.

M.p.: 212°-213° C.

Elemental analysis Calcd. for $C_{23}H_{22}ClN_5O_2$: C, 63.37; H, 5.09; N, 16.07, Found: C, 63.36; H, 5.11; N, 16.09.

EXAMPLE 33

In the same manner as Example 18(b), 2-(2-methylquinolin-4-yl)-3-piperidinocarbonylmethylisoindolin-1-one was obtained from 2-(2-methylquinolin-4-yl)-3-hydroxyisoindolin-1-one and piperidinocarbonylmethylenetriphenylphosphorane.

M.p.: 200°-202° C.

Elemental analysis Calcd. for $C_{25}H_{25}N_3O_2$: C, 75.16; H, 63.31; N, 10.52, Found: C, 75.21; H, 6.33; N, 10.46.

EXAMPLE 34

In the same manner as Example 22, 5-chloro-2-(7-chloro-1,8-naphthyridin-2-yl)-3-piperidinocarbonylmethylisoindolin-1-one was obtained from 5-chloro-3-hydroxy-2-(7-chloro-1,8-naphthyridin-2-yl)isoindolin-1-one and piperidinocarbonylmethylenetriphenylphosphorane.

M.p.: 272°–274° C.

Elemental analysis: Calcd. for $C_{23}H_{20}Cl_2N_4O_2$: C, 60.67; H, 4.43; N, 12.30, Found: C 60.54; H, 4.34; N, 12.25.

EXAMPLE 35

In the same manner as Example 22, 6-chloro-2-(7-chloro-1,8-naphthryidin-2-yl)-3-piperidinoca bonylmethylisoindolin-1-one was obtained from 6-chloro-3-hydroxy-2-(7-chloro-1,8-naphthyridin-2-yl)isoindolin-1-one.

M.p.: 295°–297° C.

Elemental analysis: Calcd. for $C_{23}H_{20}Cl_2N_4O_2$: C, 60.67; H, 4.43; N, 12.30, Found: C, 60.60; H, 4.25; N, 12.21.

EXAMPLE 36

Ethyl 6-chloro-3-oxo-2-(4-methoxyphenyl)isoindoline-1-acetate (1.0 g) and N-methylpiperazine (1.3 g) was heated at 110° C. for 4 hours in an nitrogen stream. After cooling, water (40 ml) was added to the reaction mixture and crystals separated were collected by filtration, washed with water and then dried. Recrystallization from ether gave 5-chloro-2-(4-methoxyphenyl)-3-(4-methylpiperazin-1-yl)carbonylmethylisoindolin-1-one (1.0 g). The product was identified with the compound No. 13 in Table 5 and melted at 169°–171° C.

FORMULATION EXAMPLE 1

| | | |
|---|---|---|
| (1) | 2-(4-Chlorophenyl)-3-piperidinocarbonylmethyl-isoidolin-1-one | 1 g |
| (2) | Lactose | 89 g |
| (3) | Corn starch | 29 g |
| (4) | Magnesium stearate | 1 g |
| | | 120 g for 1000 tablets |

The whole amounts of (1) and (2) and 17 g of corn starch (3) were blended and combined with a paste prepared from 7 g of corn starch. The mixture was granulated and 5 g of corn starch and the indicated amount of (4) were further added. This composition was molded on a compression tablet machine to give 1000 tablets measuring 7 mm in diameter and each containing 1 mg of (1).

FORMULATION EXAMPLE 2

| | | |
|---|---|---|
| (1) | 6-Chloro-2-(4-methoxyphenyl)-3-(4-methylpiperazin-1-yl)carbonyl-isoindolin-1-one | 2 g |
| (2) | Lactose | 88 g |
| (3) | Corn starch | 29 g |
| (4) | Magnesium stearate | 1 g |
| | | 120 g for 1000 tablets |

In the same manner as Formulation Example 1, there were produced 1000 tablets measuring 7 mm in diameter and each containing 2 mg of (1).

Reference Example 1

A solution of 56.5 g of cycloacetyl chloride in toluene (400 ml) was added to 5° C., and a solution of 85.2 g of piperidine in toluene (200 ml) was added portionwise. The mixture was stirred at 5° C. for 3 hours and at 25° C. for an hour. The resulting crystals precipitated were filtered off, 117 g of triphenylphosphine was added to the filtrate, and the mixture was heated at 80° C. for 6 hours. After cooling, the crystals precipitated were collected by filtration to give 125 g of crystals of piperidinocarbonylmethyltriphenylphosphonium chloride. This product was dissolved in 1 l of ice water and under ice-cooling 500 ml of 0.5N sodium hydroxide was added. The crystals precipitated were collected by filtration, washed with water and dried. Recrystallization from methylene chloride-ether (1:10) gave crystals (91 g) of piperidinocarbonylmethylenetriphenylphosphorane.

M.p.: 180°–188° C.

Elemental analysis Calcd. for $C_{25}H_{26}NOP$: C, 77.50; H, 9.37; N, 3.62, Found: C, 77.71; H, 9.61; N, 3.54.

REFERENCE EXAMPLE 2

In the same manner as Reference Example 1, there were obtained the following compounds:
(i) Pyrrolidinocarbonylmethylenetriphenylphosphorane M.p.: 202°–204° C.

Elemental analysis: Calcd. for $C_{24}H_{24}NOP$: C, 77.19; H, 6.48; N, 3.75, Found: C, 77.10; H, 6.58; N, 3.79.

(ii) Hexamethyleneiminocarbonylmethylenetriphenylphosphorane

M.p.: 189°–192° C.

Elemental analysis: Calcd. for $C_{26}H_{28}NOP$: C, 77.78; H, 7.03; N, 3.49, Found: C, 77.49; H, 6.96; N, 3.49.

what is claimed is:

1. A compound of the formula

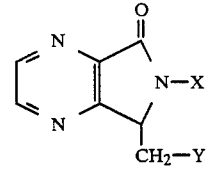

wherein X is a cyclic group of the class consisting of phenyl, naphthyl, pyridyl, pyridazinyl, pyrazinyl, pyrimidinyl, quinolyl, naphthyridinyl, thiazolyl, benzothiazolyl or $C_{3-7}$ cycloalkyl, which cyclic group is attached through a carbon atom thereof and is unsubstituted or substituted by one halogen or $C_{1-4}$ alkoxy; and Y is —COOH, —COOR$_1$ or —CO—NR$^2$R$^3$, wherein R$^1$ is $C_{1-4}$ alkyl, phenyl-$C_{1-4}$ alkyl or phenyl, and wherein R$^2$ and R$^3$ are the same or different members of the class consisting of hydrogen, $C_{1-4}$ alkyl, phenyl-$C_{1-4}$ alkyl, phenyl, thiazolyl or benzothiazolyl, which are unsubstituted or substituted by a member of the class consisting of halogen, hydroxyl, $C_{1-4}$ alkoxy, $C_{2-5}$ alkoxycarbonyl and di-$C_{1-4}$ alkylamino, or wherein NR$^2$R$^3$ is a cyclic group of the class consisting of pyrrolidinyl, piperidino, hexahydroazepinyl, piperazinyl, morpholino or thiazolidinyl, which cyclic group is unsubstituted or substituted by a member of the class consisting of hydroxyl, $C_{1-4}$ alkoxy, $C_{1-4}$ alkyl, $C_{2-5}$ alkoxycarbonyl, phenyl-$C_{1-4}$ alkyl, phenyl, piperidino and pyridyl; or pharmaceutically acceptable salts thereof.

2. A compound according to claim 1, wherein X is phenyl or pyridyl, which may be substituted by one halogen or $C_{1-4}$ alkoxy.

3. A compound according to claim 1, wherein Y is —CO—NR$^2$R$^3$, wherein R$^2$ and R$^3$ are the same or different members of the class consisting of hydrogen, $C_{1-4}$ alkyl, phenyl-$C_{1-4}$ alkyl, phenyl, thiazolyl or benzothiazolyl, which are unsubstituted or substituted by a member of the class consisting of halogen, hydroxyl, $C_{1-4}$ alkoxy, $C_{2-5}$ alkoxycarbonyl and di-$C_{1-4}$ alkylamino, or wherein $NR^2R^3$ is a cyclic group of the class consisting of pyrrolidinyl, piperidino, hexahydroazepinyl, piperazinyl, morpholino or thiazolidinyl, which cyclic group is unsubstituted or substituted by a member of the class consisting of hydroxyl, $C_{1-4}$ alkoxy, $C_{1-4}$ alkyl, $C_{2-5}$ alkoxycarbonyl, phenyl-$C_{1-4}$ alkyl, phenyl, piperidino and pyridyl.

4. A compound according to claim 1, wherein Y is $-CO-NR^2R^3$, wherein $NR^2R^3$ is a cyclic group of the class consisting of pyrrolidinyl, piperidino, hexahydroazepinyl, piperazinyl, morpholino or thiazolidinyl, which cyclic group is unsubstituted or substituted by a member of the class consisting of hydroxyl, $C_{1-4}$ alkoxy, $C_{1-4}$ alkyl, $C_{2-5}$ alkoxycarbonyl, phenyl-$C_{1-4}$ alkyl, phenyl, piperidino and pyridyl.

5. A compound according to claim 1, wherein X is phenyl which is substituted by one halogen or $C_{1-4}$ alkoxy; and Y is $-CO-NR^2R^3$ wherein $NR^2R^3$ is a cyclic group of the class consisting of pyrrolidinyl, piperidino, hexahydroazepinyl, piperazinyl, morpholino or thiazolidinyl, which cyclic group is unsubstituted or substituted by a member of the class consisting of hydroxyl, $C_{1-4}$ alkoxy, $C_{1-4}$ alkyl, $C_{2-5}$ alkoxycarbonyl, phenyl-$C_{1-4}$ alkyl, phenyl, piperidino and pyridyl.

6. A compound according to claim 1, which is 6-(5-chloro-3-pyridyl)-6,7-dihydro-7-piperidinocarbonylmethyl-5H-pyrrolo[3,4-b]pyrazin-5-one.

7. A compound according to claim 1, which is 6-(5-chloro-2-pyridyl)-6,7-dihydro-7-(4-methylpiperazin-1-yl)carbonylmethyl-5H-pyrrolo[3,4-b]pyrazin-5-one.

8. An anti-anxiety composition which comprises (a) as the active ingredient an amount sufficient to produce anti-anxiety effect of at least one compound of claim 1 and (b) a pharmaceutically acceptable carrier.

* * * * *

UNITED STATES PATENT AND TRADEMARK OFFICE
CERTIFICATE OF CORRECTION

PATENT NO.  : 4,879,293

DATED       : November 7, 1989

INVENTOR(S) : Kentaro HIRAGA et al.

It is certified that error appears in the above-identified patent and that said Letters Patent is hereby corrected as shown below:

IN THE TITLE

Change "PYRROLS[3,4-8]" to --PYRROLO[3,4-B]--.

IN THE SPECIFICATION

Between the formulas (III) and (IV) of column 3, "X-Z" should be amended to --X    Z--.

In line 25 of column 4, "Hetelocycl." should be amended to --Heterocycl.--.

In line 25 of column 8, "The reaction to" should be amended to --The reaction is--.

In line 33 of column 40, "dithino" should be amended to --dithiino--.

Signed and Sealed this

Thirtieth Day of October, 1990

*Attest:*

HARRY F. MANBECK. JR.

*Attesting Officer*      *Commissioner of Patents and Trademarks*